United States Patent [19]

Flora

[11] 4,302,500
[45] Nov. 24, 1981

[54] BREATHABLE SURGICAL ADHESIVE TAPE

[75] Inventor: Richard D. Flora, Lake Oswego, Oreg.

[73] Assignee: Shur Medical Corporation, Portland, Oreg.

[21] Appl. No.: 109,834

[22] Filed: Jan. 7, 1980

[51] Int. Cl.³ .............................................. C09U 7/02
[52] U.S. Cl. ................................... 428/284; 128/156; 156/230; 156/235; 428/286; 428/304; 428/317; 428/343; 428/354; 428/355
[58] Field of Search ............... 428/195, 198, 200, , 428/202, 204, 284, 286, 287, 296, 304, 317, 337, 343, 352, 354, 355, 914; 156/230, 235; 128/156

[56] References Cited

U.S. PATENT DOCUMENTS

| | | | |
|---|---|---|---|
| 2,191,704 | 2/1940 | Bennett | 156/230 |
| 2,559,649 | 7/1951 | Little et al. | 156/231 |
| 3,062,683 | 11/1962 | Walleberg et al. | 428/343 |
| 3,121,021 | 2/1964 | Copeland | 128/156 |
| 3,214,501 | 10/1965 | Strauss | 264/49 |
| 3,364,063 | 1/1968 | Satas | 428/343 |
| 3,632,416 | 1/1972 | Shepherd et al. | 428/245 |
| 3,645,835 | 2/1972 | Hodgson | 428/195 |
| 3,908,650 | 9/1975 | Dunshee et al. | 128/156 |
| 3,991,754 | 11/1976 | Gertzman | 128/156 |
| 4,112,177 | 9/1978 | Salditt et al. | 428/304 |

FOREIGN PATENT DOCUMENTS 1280631  7/1972  Canada .............................. 428/343

OTHER PUBLICATIONS

"Technique of Closure: Contaminated Wounds" Edlech et al., Journal of the American College of Emergency Physicians Nov./Dec. 1974, pp. 375-381.
3M Company, "Specification—3M Brand Transfer Adhesive No. 1524" OEM-Spec. 1524-1533.
3M Company, "Product Bulletin 104 OEM".

Primary Examiner—James J. Bell
Attorney, Agent, or Firm—Klarquist, Sparkman, Campbell, Leigh, Whinston and Dellett

[57] ABSTRACT

Breathable, surgical adhesive tape. The tape includes a backing formed of continuous nylon filaments which are randomly oriented in a plane and fused together at filament crossover points. Bonded to one side of the backing is a porous adhesive layer composed of fibers embedded in a planar expanse of pressure-sensitive adhesive. The fibers are sized, lengthwise, to prevent penetration into the backing, thus to limit penetration of the adhesive into the backing.

6 Claims, 5 Drawing Figures

BREATHABLE SURGICAL ADHESIVE TAPE

BACKGROUND AND SUMMARY OF THE INVENTION

The present invention relates to surgical tape, and in particular, to breathable surgical tape having substantially uniform strength in all directions.

Breathable surgical tape is gaining increasing acceptance for closure of skin incisions and wounds that formerly required stitching. When used for skin closure, the tape must have sufficient breaking strength and adhesion strength to withstand normal shear stresses and maintain wound security. The tape must also be permeable to air and water vapor, in essence, to allow the skin to "breathe". The tape should have structural characteristics which permit skin conformability, promote resistance to curling and promote delocalization of longitudinal stresses at opposed ends of the tape, as will be explained further below. Finally, the tape should resist accumulation of debris on its outer side.

A general object of the present invention is to provide a breathable surgical adhesive tape having the desired tape characteristics mentioned above.

More specifically, it is an object to provide such tape having a breathable, unitized filamentous backing which is strong in all dimensions, is skin comformable, resists curling and promotes delocalization of longitudinal stresses in the tape.

Another object of the invention is to provide such tape having a backing laminated with a porous adhesive layer which is permeable to air and moisture and provides good adhesive strength.

Still another object of the invention is to provide such tape wherein the adhesive layer, which is somewhat fluidic, is substantially confined to one side of the tape backing.

Yet another object is to provide a method of forming a surgical tape having the above characteristics.

These objects are realized in a surgical tape having a backing formed of continuous polymeric filaments which are randomly oriented in a plane, and fused together at filament crossover points. Adhesively bonded to the filaments in the backing, on one side thereof, is a porous layer of pressure-sensitive adhesive.

In a preferred embodiment of the invention, the backing is composed of nylon filaments which are fused together in a molten state. The spacing between adjacent filaments is generally less than a specified dimension, preferably about 10 to 15 mils. The adhesive layer is composed of fibers embedded in a planar expanse of pressure-sensitive adhesive, these fibers having lengths substantially gretaer than the above-mentioned interfilament spacing dimension, thus to limit penetration of the adhesive layer into the backing.

Also disclosed herein is a method for forming a tape having the above-described structure and characteristics.

These and other objects of the present invention will become more fully apparent when read in connection with the following detailed description of the invention, and the accompanying drawings, wherein.

DETAILED DESCRIPTION OF A PREFERRED EMBODIMENT OF THE INVENTION

Figure 1:
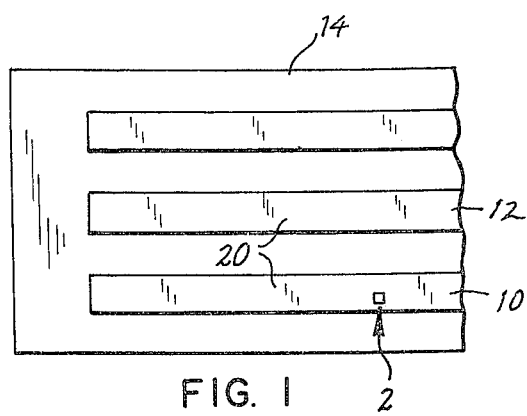
FIG. 1 is a plan view of a tape liner carrying thereon a plurality of tape strips constructed according to an embodiment of the present invention and shown here approximately in actual size.
Figure 2:
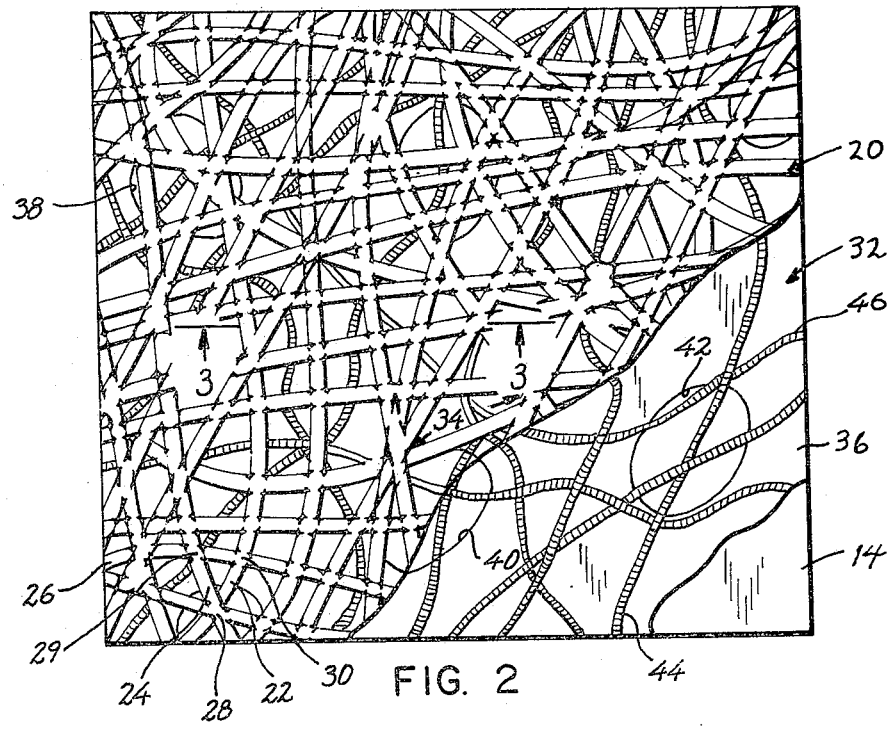
FIG. 2 is a plan view of an area of tape, indicated at 2 in FIG. 1, magnified approximately eighty times, and shown here with parts cut away.

FIG. 1 shows in plan view fragmentary portions of tape strips, such as strips 10, 12, each of which are carried, in easily dispensible form, on a non-stick silicone liner 14. Each strip, such as strip 10, is formed of tape constructed according to the present invention. Very generally, and with reference to FIGS. 2-4, the tape includes a permeable backing 20 formed of continuous filaments, such as filaments, 22, 24, 26, which are substantially randomly oriented in a plane, as seen in FIG. 2. The filaments are fused together at filament crossover points. Beonded to one side of backing 20, in a manner to be explained, is a porous layer 32 of pressure-sensitive adhesive, which can be seen best in FIG. 4.

Looking now at details of backing 20, and with reference first to FIG. 2, filaments, such as filaments 22, 24, 26 forming this backing are substantially continuous, polymeric filaments formed conventionally, such as by extrusion. The filaments are substantially randomly oriented, and loosely interlaced, whereby each filament crosses over, above and below a plane containing the backing, multiple other nonparallel filaments.

Crossover points between filaments 22, 24, between filaments 24, 26, and between filaments 22, 26, are indicated at 28, 29, 30, respectively, in FIG. 2. The space between adjacent filaments, such as filaments 22, 24, is variable, with a typical larger spacing dimension indicated at 34 in FIG. 2. According to an important constructional feature of backing 20, the filaments, such as filaments 28, 30, 32 are fused one to another, at their crossover points, by heat. Such fusion, in effect, melds the filaments together whereby the strength of the fused bond joining filaments is substantially as great as the strength of the filaments themselves. Accordingly, the unitized backing has a substantially equal strength and tear-resistance in all directions. Other important tape features inherent in backing 20 are discussed below.

Backing 20 may be formed, in one method, by laying down precooled filaments in a random pattern, such as that shown in FIG. 2, and subjecting the interlaced filaments to heat sufficient for interfilament fusing. This technique is suitable for themoplastic polymeric filaments. A second method by which backing 20 can be formed is by extrusion of molten polymeric filaments in a random pattern, such as shown in FIG. 2, with filament fusion occurring before the just-formed filaments are cooled.

One preferred backing is a self-bonded nylon fabric which is commercially available under the trade name Cerex, a product of the Monsanto Company. This product is formed from 100% nylon filaments which are self-bonded directly from molten polymer. The average filament diameter in this material is between about 1.5 and 2 mils. A larger filament spacing, corresponding to spacing 34 shown in FIG. 2, is between about 10 and 15 mils. Cerex backing having weights of between 0.5 and 1.5 ounces per square yard, and corresponding average thicknesses of between about 3 and 7 mils, respectively, has been found to possess both the desired strength and skin conformability.

Figure 3:
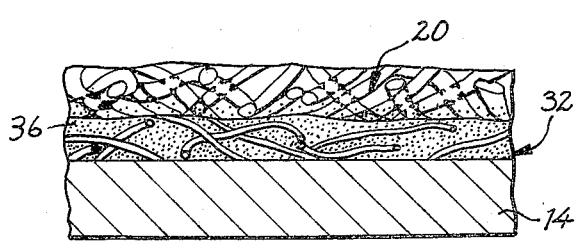
FIG. 3 is a sectional view taken generally along line 3—3 in FIG. 2.
Figure 4:
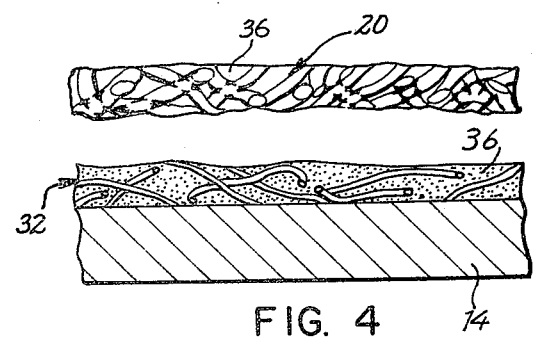
FIG. 4 is a view similar to FIG. 3, showing the sectional appearance of tape components just prior to lamination by the method of the invention.

Referring to FIGS. 2–4, layer 32 generally includes a planar expanse of pressure-sensitive adhesive 36 which is supplied as a coating on liner 14. The adhesive preferably is a tacky, semi-fluidic, large molecular weight, water insoluble, pressure-sensitive adhseive. Such adhesives, which are also translucent and hypoallergenic, are available commercially. Layer 32 is intrinsically porous, having plural pores, such as pores 38, 40, 42 seen in FIG. 2, extending therethrough. Typical pore sizes range, in their side-to-side dimensions, between about 100 to 400 microns. The pores are randomly distributed in the adhesive layer, with a typical interpore spacing of between about 0.5 and 2 millimeters.

Embedded in adhesive 36 are plural elongate polymeric fibers, such as fibers 44, 46 seen in FIG. 2. As seen particularly in FIG. 4, these fibers are essentially submerged, in non-bonded form, in the semi-fluidic adhesive. According to an important feature of the present invenion, fibers, such as fibers 44, 46, act to prevent penetration of adhesive 36 into backing 20, when the backing and adhesive layer are laminated to form the tape, as will be explained below. To this end, the lengths of the fibers in the adhesive are substantially longer than a large interfilament spacing, such as spacing 34, in backing 20. In the embodiment described herein, the fibers are substantially continuous filament fibers, as seen in FIG. 2.

Having described the tape of the present invention, important performance characteristics thereof will not be discussed. Particularly, characteristics relating to breaking strength, shear adhesion, air porosity, transmission of water vapor, resistance to curling and ability to delocalize longitudinal stresses will be emphasized. Tape used in the following tests was formed of Cerex backing having a fabric weight of 1 ounce per square yard and, laminated thereto, an adhesive layer having the characteristics described with reference to layer 32.

In determing breaking strength, a ½ inch wide strip of tape was mounted in an Instron TTM tensile tester having a gauge length of 4.5 cm. The tape was loaded with continuous increasing mass-equivalents until tape breakage occurred, characteristically, at about 4 kilograms. This breaking strength is comparable to other surgical adhesive tapes currently available.

Shear adhesion was measured by applying 1 inch length of ½ inch tape to skin, and attaching test clips to a ½ inch tape tab not adhered to the skin. The clips were attached to a strain gauge calibrated to record the mass-equivalent necessary to dislodge the tape from the skin. The shear adhesion, as measured by this test, was about 1.5 kg. This figure is also comparable to other surgical tapes currently on the market.

Air porosity was determined using a Gurley densometer.

The time necessary for 10 cc of air under constant pressure to pass through a ½ inch×½ inch orifice covered with the test tape was measured. An air porosity of about 3 cubic feet per minute per square feet was measured. Significantly, this value is 3 to 4 times greater than the similarly measured air porosities of competitive surgical tapes. The air porosity of Cerex backing having a fabric weight of 1 ounce per square yard is approximately 350 cubic feet per minute per square foot (Monsanto technical bulletin no. 14-328-0377-6). Thus, air flow through the tape is largely determined, or rate limited, by the porosity of the adhesive layer.

Moisture vapor transmission was determined by a MEECO electrolytic moisture analyzer (Model W, Manufactureres Engineering and Equipment Corporation). Vapor transmission was measured as water vapor increase in dry air as the air passed over a controlled area of tape which was in direct contact with liquid water. Under these test conditions, the tape transmitted approximately 70 $\mu$l/per minute per square centimeter of tape. This value is comparable to, or better than, the moisture vapor transsision of other commercially available surgical tapes.

Figure 5:
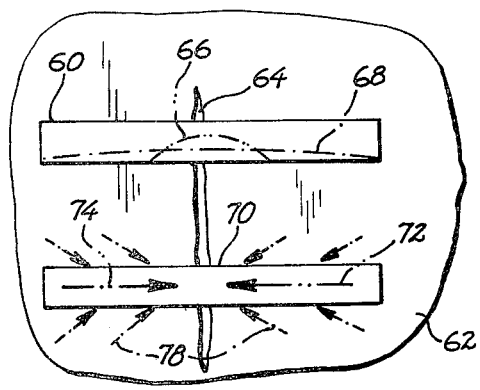
FIG. 5 shows tape strips, such as in FIG. 1, applied to a section of skin containing a wound, illustrating the tape's resistance to curling and delocalization of longitudinal stresses, as will be explained.

Considering now the tape's resistance to curling, in FIG. 5 there is shown at 60 a tape strip adhesively attached to a section of skin 62, to close an incision 64. In some prior art surgical tapes, slight pressure, such as finger pressure, applied to the tape, in this case upwardly in the figure, in the direction of the incision, produces tape curling, as indicated by dash-double-dot line 66 in FIG. 5, which seriously affects the wound-protecting area of the tape. In the tape of the present invention, the continuous interbonded filaments in the tape backing transmit forces applied to a local edge portion of the tape throughout its length. As indicated by the dash-dot line at 68 in FIG. 5, such tends to produce slight folding along the entire tape edge in the direction of the applied force, with wound security being substantially preserved.

A second tape strip 70 shown in FIG. 5 is intended to illustrate the interaction between the skin and tape when the tape is used for wound closure. As noted above, a surgical tape strip functions to hold two sides of a wound in a closed position, and thus must be stretched somewhat tightly on the skin on either side of the wound. This produces forces in the tape, indicated by dash-double-dot arrows 72, 74, which draw opposed end portions of the tape inwardly. In prior art surgical tape, such forces are directed substantially longitudinally, causing skin regions, adjacent the two ends of the tape, to be severely, and locally stretched. Over the period of several days required for wound healing, such can produce soreness and blistering in the stretched skin regions.

It can be appreciated with reference to FIG. 2, that in a fabric composed of unitized, randomly oriented substantially continuous filamnets, a force applied to the backing in one direction produces a distribution of that force in a plurality of different directions, essentially delocalizing a unidirectional force applied to the backing. Referring again to FIG. 5, it can be appreciated how forces 72, 74 in the tape of the present invention are redistributed as forces acting somewhat inwardly substantially along the tape's two side edges, as indicated by arrows, such as arrows 78. As a result, skin distortion is distributed somewhat uniformly along the entire length of the tape to minimize just-mentioned problems of prior art tapes.

Turning now to the method of forming the instant tape, and with attention directed to FIG. 4, backing 20 is laminated to layer 32, with the latter coating liner 14, by feeding matched strips of backing and adhesive-coated liner through pressure rollers of the like. As noted above, the adhesive used in forming layer 18 is somewhat fluidic and thus tends to be squeezed into the backing matrix during tape formation. According to an important feature of the invention, the fibers in layer 32 provide a substantially incompressable bulk which tends to keep the fluidic adhesive material somewhat sequestered during tape lamination. After tape formation, the tendency of the fluidic adhesive material to flow into the backing is resisted by the bulk effect of the fibers in limiting adhesive flow. Explaining further, the adhesive tends toward an equilibrium wherein the adhesive is distributed on fibers in the adhesive layer and filaments in the backing. At this equilibium, the adhesive penetrates only slightly into the backing.

Advantages of tape formed by the just-described method are readily apparent. The lamination step is quite simple, and preserves the pores contained in the adhesive layer. By contrast, commonly in the prior art, an adhesive is applied as a liquid coating to one side of a tape backing, wherein pores in the adhesive must be created, subsequently, as by controlled heating. Another important advantage of the lamination method of the present invention is the capability of controlling and limiting the extent of penetration of adhesive into the backing. Such controlling is accomplishable by varying the laminating conditions, such as roller pressure, or by varying the ratio of adhesive to fibers in the adhesive layer. As a result, more adhesive is carried on the adhesive of the tape, to improve the tape's shear adhesion properties. The tape also tends to stay cleaner on its nonadhesive side because of the absence of adhesive material near the exposed surface of the tape.

From the above, it can be appreciated how the various objects of the tape of the present invention are met. First, the tape provides sufficient breaking and shear adhesion strength for its use for closure of skin incisions. The tape is able to transmit moisture, thus to prevent moisture accumulation under the tape, and further has exceptional air porosity characteristics, both of the latter properties helping to promote skin healing and reduce proliferation of bacteria. Two particularly advantageous features of the tape are related to the unitized, randomly oriented, filamentous nature of the tape backing, which enhance the tape's resistance to curling and the ability of the tape, when stretched across a wound, to transmit stretching forces along the side edges of the tape. Finally, the method of the present invention, which includes selecting an adhesive layer composed of fibers embedded in a planar expanse of pressure-sensitive adhesive, and laminating this layer to a self-bonded filamentous backing, produces a tape with desired porosity, and adhesion characteristics.

While a specific embodiment of a breathable surgical adhesive tape used in closure of skin incisions, and a method of forming this tape, have been disclosed herein, it is obvious that various changes and modifications may be made without departing from the spirit of the invention.

It is claimed and desired to secure by letters patent:

1. Breathable, surgical adhesive tape comprising:
a permeable backing strip sufficiently strong to hold a wound closed when the tape is applied to skin of a human or other animal subject, the backing strip being formed of substantially continuous polymeric filaments which
   (a) are substantially randomly oriented in a plane,
   (b) define open spaces through the strip, and
   (c) are secured together at crossover points; and
an adhesive strip comprising a layer of pressure-sensitive adhesive bonded to the backing strip, on one side thereof, and forming a laminate therewith, the adhesive strip having a plurality of pores positioned randomly with respect to the open spaces through the backing strip.

2. A method of forming a breathable surgical adhesive tape comprising:
selecting a permeable backing strip sufficiently strong to hold a wound closed when the tape is applied to the skin of a human or other animal subject, the backing strip being formed of continuous polymeric filaments which are substantially randomly oriented in a plane and secured together at fiber crossover points;
selecting an adhesive strip comprising a layer carried on one side of a non-stick liner, such layer being composed of an intrinsically porous planar expanse of pressure-sensitive adhesive;
longitudinally aligning the backing strip and the adhesive strip; and
pressing the layer against one side of said backing strip to bond the former to the latter.

3. The method of claim 2 wherein:
the backing strip is selected such that the filaments define open spaces through the backing strip;
the adhesive strip is selected such that it has a plurality of pores; and
the layer is pressed against the one side of the backing strip such that the spaces are positioned randomly with respect to the pores after the pressing.

4. Breathable, surgical adhesive tape comprising:
a permeable backing strip sufficiently strong to hold a wound closed when the tape is applied to the skin of a human or other animal subject, the backing strip being formed of continuous polymeric filaments which are substantially randomly oriented in a plane, and secured together at crossover points, the distance between adjacent fibers being generally less than a specified dimension; and
bonded to one side of the backing strip and forming a laminate therewith, an adhesive strip composed of fibers embedded in a porous planar expanse of pressure-sensitive adhesive, the fibers having lengths substantially greater than the specified dimension to prevent fiber penetration into the backing strip and to inhibit penetration of the adhesive into the backing strip, whereby to inhibit long-term storage problems resulting from cold flow, such as the development of adhesive tackiness on the other side of the backing strip, degradation of adhesive strength and degradation of tape porosity.

5. The tape of claim 4, wherein said specified dimension is between about 10 and 15 mils.

6. A method of forming a breathable surgical adhesive tape comprising:
selecting a permeable backing strip formed of continuous polymeric filaments which are substantially randomly oriented in a plane and secured together at fiber crossover points, with the spacing between adjacent fibers being generally less than a specified dimension;
selecting an adhesive strip comprising a layer carried on one side of a non-stick liner, with such layer being composed of fibers embedded in a porous planar expanse of pressure-sensitive adhesive, and with such fibers having lengths substantially greater than such specified dimension;
longitudinally aligning the backing strip and the adhesive strip; and
pressing the layer against one side of said backing strip to bond the former to the later, the fibers, because of their relatively great lengths, serving to inhibit penetration of the adhesive into said backing.

* * * * *

UNITED STATES PATENT AND TRADEMARK OFFICE
CERTIFICATE OF CORRECTION

PATENT NO. : 4,302,500
DATED : November 24, 1981
INVENTOR(S) : Richard D. Flora

It is certified that error appears in the above—identified patent and that said Letters Patent is hereby corrected as shown below:

Column 3, line 25, "invenion" should read -- invention --.

Column 3, line 35, "not" should read -- now --.

Column 3, line 44, "determing" should read -- determining --.

Column 3, line 62, "1/2 inch x 1/2 inch" should read -- 1/2 inch x 1/4 inch --.

Column 4, line 65, "of" should read -- or --.

Column 5, line 25, "sive of the tape" should read -- sive side of the tape --.

Signed and Sealed this

Thirteenth Day of April 1982

[SEAL]

Attest:

Attesting Officer

GERALD J. MOSSINGHOFF

Commissioner of Patents and Trademarks